(12) United States Patent
Smith et al.

(10) Patent No.: US 8,673,012 B2
(45) Date of Patent: Mar. 18, 2014

(54) INTERVERTEBRAL SPACER AND INSERTION TOOL PROVIDING MULTIPLE ANGLES OF INSERTION

(75) Inventors: Colin M. Smith, Dana Point, CA (US); Leah Schermerhorn, San Diego, CA (US)

(73) Assignee: SeaSpine, Inc., Vista, CA (US)

( * ) Notice: Subject to any disclaimer, the term of this patent is extended or adjusted under 35 U.S.C. 154(b) by 0 days.

(21) Appl. No.: 13/543,672

(22) Filed: Jul. 6, 2012

(65) Prior Publication Data

US 2012/0277877 A1  Nov. 1, 2012

Related U.S. Application Data

(63) Continuation of application No. 11/371,539, filed on Mar. 8, 2006, now abandoned.

(51) Int. Cl.
*A61F 2/44* (2006.01)

(52) U.S. Cl.
USPC ............................................ 623/17.16

(58) Field of Classification Search
USPC .......................................... 623/17.11–17.16
See application file for complete search history.

(56) References Cited

U.S. PATENT DOCUMENTS

| | | | |
|---|---|---|---|
| 5,071,437 A | 12/1991 | Steffee | |
| 5,431,658 A | 7/1995 | Moskovich | |
| 5,676,701 A | 10/1997 | Yuan et al. | |
| 5,733,290 A | 3/1998 | McCue et al. | |
| 5,755,796 A | 5/1998 | Ibo et al. | |
| 5,899,941 A | 5/1999 | Nishijima et al. | |
| 6,033,438 A | 3/2000 | Bianchi et al. | |
| 6,113,637 A | 9/2000 | Gill et al. | |
| 6,113,638 A | 9/2000 | Williams et al. | |
| 6,193,757 B1 | 2/2001 | Foley et al. | |
| 6,206,924 B1 | 3/2001 | Timm | |
| 6,235,059 B1 | 5/2001 | Benezech et al. | |
| 6,319,257 B1 | 11/2001 | Carignan et al. | |
| 6,368,350 B1 | 4/2002 | Erickson et al. | |
| 6,368,354 B2 | 4/2002 | Burstein et al. | |
| 6,478,801 B1 | 11/2002 | Ralph et al. | |
| 6,572,619 B2 | 6/2003 | Santilli | |
| 6,595,998 B2 | 7/2003 | Johnson et al. | |
| 6,673,075 B2 | 1/2004 | Santilli | |
| 6,699,288 B2 | 3/2004 | Moret | |
| 6,736,849 B2 | 5/2004 | Li et al. | |

(Continued)

FOREIGN PATENT DOCUMENTS

DE    2263842    7/1974

OTHER PUBLICATIONS

Hoffman-Daimler, Invertebral Disk Displacement, vol. 112, No. 4, Aug. 1974.

(Continued)

*Primary Examiner* — Sameh Boles
(74) *Attorney, Agent, or Firm* — James W. Hill; McDermott Will & Emery LLP

(57) ABSTRACT

An intervertebral spacer can have a leading end and a trailing end that includes an engaging portion configured to securely engage complementary features of an insertion tool at any of a plurality of different angles. The engaging portion can have a first radius and a major axis extending from the leading end to the trailing end. The trailing end can have a channel formed around a partially cylindrical portion having a second radius that is less than the first radius. The channel can be configured to accept an extending portion of the insertion tool.

25 Claims, 12 Drawing Sheets

(56) References Cited

U.S. PATENT DOCUMENTS

| | | |
|---|---|---|
| 6,743,257 B2 | 6/2004 | Castro |
| 6,758,862 B2 | 7/2004 | Berry et al. |
| 6,793,678 B2 | 9/2004 | Hawkins |
| 6,800,092 B1 | 10/2004 | Williams et al. |
| 6,805,714 B2 | 10/2004 | Sutcliffe |
| 6,866,929 B2 | 3/2005 | Kodas et al. |
| 6,899,735 B2 | 5/2005 | Coates et al. |
| 6,964,686 B2 | 11/2005 | Gordon |
| 6,966,932 B1 | 11/2005 | Schroeder |
| 6,974,480 B2 | 12/2005 | Messerli et al. |
| 7,048,764 B2 | 5/2006 | Ferree |
| 7,156,876 B2 | 1/2007 | Moumene et al. |
| 7,198,643 B2 | 4/2007 | Zubok et al. |
| 7,217,293 B2 | 5/2007 | Branch, Jr. |
| 7,235,101 B2 | 6/2007 | Berry et al. |
| 7,250,060 B2 | 7/2007 | Trieu |
| 7,276,082 B2 | 10/2007 | Zdeblick et al. |
| RE40,260 E | 4/2008 | Buhler |
| 7,503,933 B2 | 3/2009 | Michelson |
| 7,517,363 B2 | 4/2009 | Rogers et al. |
| 7,537,612 B2 | 5/2009 | Kunzler |
| 7,563,284 B2 | 7/2009 | Coppes et al. |
| 7,575,580 B2 | 8/2009 | Lim et al. |
| 7,606,068 B2 | 10/2009 | Shieh et al. |
| 2001/0020170 A1 | 9/2001 | Zucherman et al. |
| 2003/0045939 A1 | 3/2003 | Casutt |
| 2003/0069586 A1 | 4/2003 | Errico et al. |
| 2004/0097929 A1 | 5/2004 | Branch et al. |
| 2004/0167538 A1 | 8/2004 | Gerber et al. |
| 2004/0243241 A1 | 12/2004 | Istephanous et al. |
| 2005/0027360 A1 | 2/2005 | Webb et al. |
| 2005/0038431 A1 | 2/2005 | Bartish et al. |
| 2005/0038516 A1 | 2/2005 | Spoonamore |
| 2005/0143822 A1 | 6/2005 | Paul |
| 2006/0149273 A1 | 7/2006 | Ross et al. |
| 2006/0229627 A1 | 10/2006 | Hunt et al. |
| 2006/0229729 A1 | 10/2006 | Gordon et al. |
| 2007/0093897 A1 | 4/2007 | Gerbec et al. |
| 2007/0162128 A1 | 7/2007 | DeRidder et al. |
| 2007/0162138 A1 | 7/2007 | Heinz |
| 2007/0213826 A1 | 9/2007 | Smith et al. |
| 2007/0225808 A1 | 9/2007 | Warnick |
| 2008/0009880 A1 | 1/2008 | Warnick et al. |
| 2008/0051890 A1 | 2/2008 | Waugh et al. |
| 2008/0077153 A1 | 3/2008 | Pernsteiner et al. |
| 2008/0077247 A1 | 3/2008 | Murillo et al. |
| 2008/0275506 A1 | 11/2008 | Baynham et al. |
| 2009/0082868 A1 | 3/2009 | Cordaro et al. |
| 2010/0030270 A1 | 2/2010 | Winslow et al. |

OTHER PUBLICATIONS

Trouillier, H., et al., "Report on Two Failed Posterior Lumbar Interbody Fusions," SICOT Online Report E034: Accepted May 6, 2003, Department of Orthopedic Surgery, Institute of Pathology, Ludwig-Maximilians University, Munich, Germany, pp. 1-12.

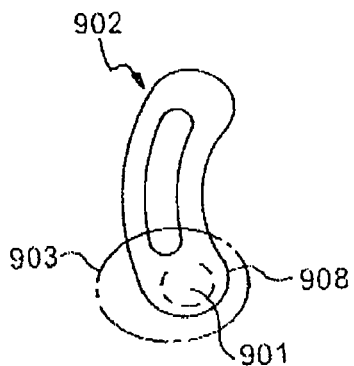
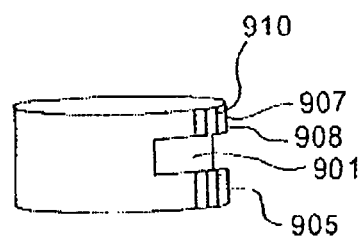
FIG. 9A  FIG. 9B
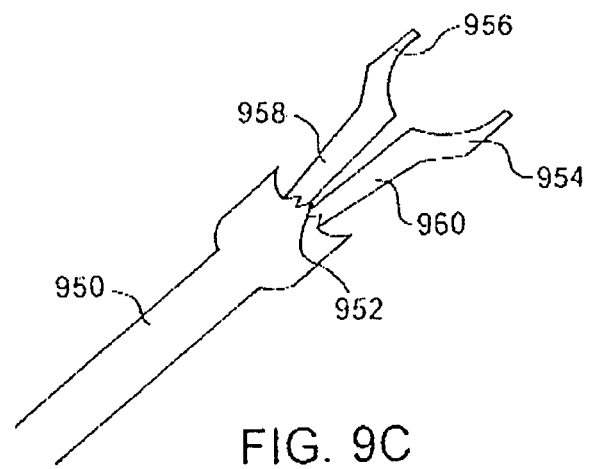
FIG. 9C

INTERVERTEBRAL SPACER AND INSERTION TOOL PROVIDING MULTIPLE ANGLES OF INSERTION

CROSS REFERENCE TO RELATED APPLICATION

The present application is a continuation of U.S. patent application Ser. No. 11/371,539, filed Mar. 8, 2006, the entirety of which is incorporated herein by reference.

FIELD

The present invention relates, in general, to artificial prosthetics and, more particularly, to intervertebral spacers.

BACKGROUND

A normal human spine is segmented with seven cervical, twelve thoracic and five lumbar segments. The lumbar portion of the spine resides on the sacrum, which is attached to the pelvis. The pelvis is supported by the hips and leg bones. The bony vertebral bodies of the spine are separated by intervertebral discs, which reside sandwiched between the vertebral bodies and operate as joints allowing known degrees of flexion, extension, lateral bending and axial rotation.

The intervertebral disc primarily serves as a mechanical cushion between adjacent vertebral bodies, and permits controlled motions within vertebral segments of the axial skeleton. The disc is a multi-element system, having three basic components: the nucleus pulposus ("nucleus"), the anulus fibrosus ("anulus") and two vertebral end plates. The end plates are made of thin cartilage overlying a thin layer of hard, cortical bone that attaches to the spongy, richly vascular, cancellous bone of the vertebral body. The plates thereby operate to attach adjacent vertebrae to the disc. In other words, a transitional zone is created by the end plates between the malleable disc and the bony vertebrae.

The anulus of the disc forms the disc perimeter, and is a tough, outer fibrous ring that binds adjacent vertebrae together. The fiber layers of the anulus include fifteen to twenty overlapping plies, which are inserted into the superior and inferior vertebral bodies at roughly a 40 degree angle in both directions. This causes bi-directional torsional resistance, as about half of the angulated fibers will tighten when the vertebrae rotate in either direction.

It is common practice to remove a spinal disc in cases of spinal disc deterioration, disease or spinal injury. The discs sometimes become diseased or damaged such that the intervertebral separation is reduced. Such events cause the height of the disc nucleus to decrease, which in turn causes the anulus to buckle in areas where the laminated plies are loosely bonded. As the overlapping laminated plies of the anulus begin to buckle and separate, either circumferential or radial anular tears may occur. Such disruption to the natural intervertebral separation produces pain, which can be alleviated by removal of the disc and maintenance of the natural separation distance. In cases of chronic back pain resulting from a degenerated or herniated disc, removal of the disc becomes medically necessary.

In some cases, the damaged disc may be replaced with a disc prosthesis intended to duplicate the function of the natural spinal disc. In other cases it is desired to fuse the adjacent vertebrae together after removal of the disc, sometimes referred to as "intervertebral fusion" or "interbody fusion."

In cases of intervertebral fusion, it is known to position a spacer centrally within the space where the spinal disc once resided, or to position multiple spacers within that space. Such practices are characterized by certain disadvantages, including a disruption in the natural curvature of the spine. For example, the vertebrae in the lower "lumbar" region of the spine reside in an arch referred to in the medical field as having a sagittal alignment. The sagittal alignment is compromised when adjacent vertebral bodies that were once angled toward each other on their posterior side become fused in a different, less angled orientation relative to one another.

While the occurrence of successful spinal surgeries of any of the variety mentioned above has greatly improved in recent years, there continue to be challenges and room for improvement in the area of intervertebral spacers and prosthetics. In particular, a patient's precise anatomy is often not known prior to surgery although general predictions will be available. Additionally, while surgery is a well-planned process, not all conditions can be known beforehand and some variations will likely not be ideal. Accordingly, during surgery a surgeon will likely need to make decisions that balance speed, safety, and efficacy. One such decision can relate to the approach angle at which the spacer is inserted into the patient's body. This angle can vary either anteriorly or posteriorly from a lateral approach depending on the surgical conditions encountered. A spacer that is adaptable to the wide vagaries of surgical conditions that might be encountered will provide many benefits to patients and surgeons. Presently, many intervertebral spacers require an insertion tool that fixedly threads into the spacer's body thereby limiting the alignment between the tool and the spacer to a single position. Thus, there remains a need for intervertebral spacers that offer the surgeon more ease-of-use and flexibility than the spacers that are currently available.

SUMMARY

One aspect of the present invention relates to an intervertebral spacer that includes a leading end and a trailing end. The trailing end is configured to accept therein an extending portion of an insertion tool, wherein the trailing end includes an external surface configured to securely engage a complementary surface of the insertion tool at a plurality of different angles.

Another aspect of the present invention relates to an intervertebral spacer that includes a trailing end configured to engage an insertion tool at an angle. Within this aspect, the trailing end includes a first portion configured to securely receive an extending portion of the insertion tool, and a second portion having a surface shaped to engage a complementary-shaped surface of the insertion tool at a plurality of different positions such that the angle differs for each of the different positions.

Yet a further aspect of the present invention relates to a method for using an intervertebral spacer. In accordance with this method, an extending portion of an insertion tool is received within the intervertebral spacer; and a first surface of the intervertebral spacer is securely engaged with a second surface of the insertion tool in one of a plurality of different positions, while the extending portion is disposed within the intervertebral spacer.

It is understood that other embodiments of the present invention will become readily apparent to those skilled in the art from the following detailed description, wherein it is shown and described only various embodiments of the invention by way of illustration. As will be realized, the invention is capable of other and different embodiments and its several details are capable of modification in various other respects, all without departing from the spirit and scope of the present invention. Accordingly, the drawings and detailed description are to be regarded as illustrative in nature and not as restrictive.

BRIEF DESCRIPTION OF THE DRAWINGS

Various aspects of an intervertebral spacer and insertion tool are illustrated by way of example, and not by way of limitation, in the accompanying drawings, wherein:

FIG. 7 depicts a detailed view of another trailing end of a spacer; and.

FIGS. 9A-9C depict another alternative intervertebral spacer and insertion tool.

DETAILED DESCRIPTION

The detailed description set forth below in connection with the appended drawings is intended as a description of various embodiments of the invention and is not intended to represent the only embodiments in which the invention may be practiced. The detailed description includes specific details for the purpose of providing a thorough understanding of the invention. However, it will be apparent to those skilled in the art that the invention may be practiced without these specific details. In some instances, well known structures and components are shown in block diagram form in order to avoid obscuring the concepts of the invention.

Figure 1:
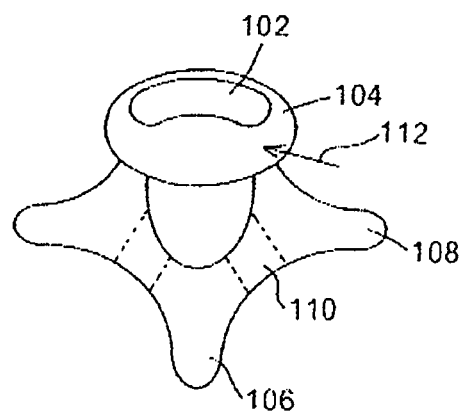
FIG. 1 depicts a intervertebral spacer arranged on a vertebrae body in accordance with the principles of the present invention.

FIG. 1 illustrates one typical environment in which intervertebral spacers may be used in accordance with the principles of the present invention. The spacer 102 is shown on top of a vertebrae body 104. The spinous process 106 is located posteriorly with respect to the body 104. The transverse process 108 and the lamina 110 are located between the body 104 and the spinous process 106. The second vertebrae body which sits over top of the spacer 102 is not shown in FIG. 1 for purposes of clarity. However, as is well known to one of ordinary skill, the spacer 102 is used in this manner to separate two adjacent vertebrae bodies.

The spacer 102 of FIG. 1 is generally kidney-shaped and includes contours that roughly follow the shape of the vertebrae body 104. For purposes of orientation, the posterior portion of the spacer 102 is located closer to the spinous process 106 and the anterior portion is located away from the spinous process 106. This orientation is for purposes of providing a consistent frame of reference and is not intended to be interpreted as a limitation of the present invention.

The spacer 102 may be used in a variety of configurations; however, the configuration of FIG. 1 is a typical configuration with the spacer 102 located near the anterior region of the vertebrae body 104. During surgery, a surgeon will place the spacer at this location and may do so using a variety of techniques. In particular, the arrow 112 indicates a direction generally referred to, with respect to spacer implants, as transforaminal. This arrow 112 shows the general direction at which the spacer 102 is inserted between two adjacent vertebrae bodies. Advantageous attributes of the present invention allow this direction 112 to widely vary, even during surgery, to allow a surgeon great flexibility in inserting the spacer 102. Furthermore, the orientation of the major axis of the spacer relative to the direction 112 may vary as well.

Because the spacer 102 is designed for insertion in a patient's body, its material is selected to withstand such an environment without deteriorating or harming the patient. Exemplary materials useful in these types of circumstances include, but are not limited to, polyether ether ketone, titanium, artificial bone material, and natural bone tissue. Other similar material may be used without departing from the scope of the present invention.

FIGS. 2A-2E show different views of a more detailed depiction of the spacer 102. A number of the features described with reference to these figures are optional but provide advantages recognized in the art of intervertebral spacers. For example, holes may be present that permit the insertion of bone-grafting material that helps fuse the spacer to adjacent spinal bodies. Also, the spacer surfaces which are adjacent vertebrae bodies may be rough, or otherwise "keyed", to improve the mechanical adherence of the spacer to the bodies. In this way, the spacer is less likely to move or shift once it has been surgically implanted.

Figure 2A:
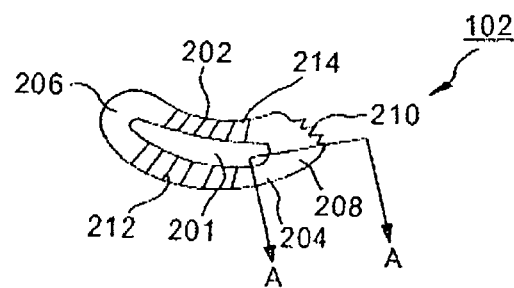
FIGS. 2A-2F depict various views of the intervertebral spacer of FIG. 1.

FIG. 2A depicts a view from the superior side of the spacer 102. From this view, the spacer 102 can be seen as a kidney-shaped cage having a central cavity 201. As mentioned previously, this cavity 201 may be filled with bone-grafting material if desired. The spacer 102 includes a posterior side 202 and an anterior side 204. Each of these sides extends from a leading end 206 to a trailing end 208. The top of the posterior side 202 is shown having teeth, or ridges, 214; while the top of the anterior side 204 is shown with similar teeth 212.

These teeth 212, 214 are exemplary in nature and can vary in numerous ways, or even be absent, without departing from the scope of the present invention. For example, the teeth 212, 214 may be pointed at their peaks and have rounded, pointed, or squared valleys between adjacent peaks. The slope of the sides of the teeth 212, 214 may vary as well as the spacing between the teeth 212, 214. Similarly, the height of the teeth 212, 214 may vary as well. Because the posterior side 202 and anterior side 204 may be arcuate shaped, the teeth may be spaced variably such that they are closer at their posterior side end that at their anterior side end.

An exemplary embodiment contemplated within the scope of the present invention includes teeth 214 on the posterior side that are spaced about every 10 degrees and have a height of approximately 0.030 inches. In particular, the sides of adjacent teeth 214 adjoin one another at the bottom and form a 90 degree angle with one another. Similarly shaped teeth 212 may be located on the anterior side 204 but spaced at approximately every 5 degrees.

The trailing end 208 includes an exterior surface 210 that has a shape and other features that will be described in more detail later. In general, though, the surface 210 includes engaging surfaces shaped to actively engage a complementary-shaped engaging surface of an insertion tool.

Figure 2B:
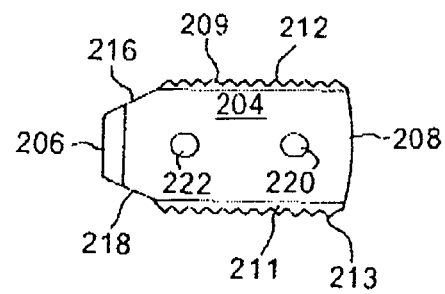

FIG. 2B is a view of the anterior side 204 and shows a superior side 209 and inferior side 211. These sides 209, 211 generally form the top surface and bottom surface of the spacer 102. The teeth 212 can also be seen that are on the superior side 209 of the anterior side 204. Similar teeth 213 may also be present on the inferior side 211 of the anterior side 204. Holes 220 and 222 may be used to provide access for bone-grafting material or other substances to be injected into the spacer 102 or may allow for vascularization after implantation. From this view, sloped sides of the 216 and 218 are also visible. These sloped areas of the superior and inferior sides near the leading end 206 are not necessary but may be included in the spacer 102 to assist with insertion of the spacer 102 between adjacent vertebrae bodies.

Figure 2C:
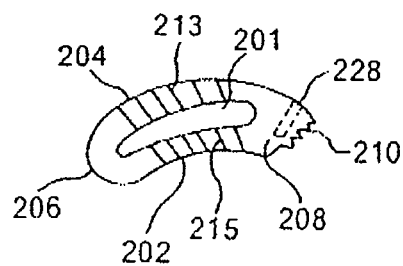

FIG. 2C depicts a view from the inferior side of the spacer 102. As shown, teeth 215 may be formed on the inferior side of the posterior side 202. These teeth 215 are similar to previously discussed teeth 212, 214 and the other teeth as well. As mentioned before, the size, shape, and placement of the teeth may vary greatly without departing from the scope of the present invention. However, in one embodiment, they may be sized similar to the teeth described with respect to FIG. 2A.

Figure 2D:
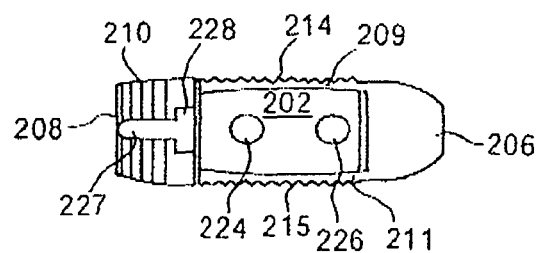

FIG. 2D depicts a view of the posterior side 202 of the spacer 102. The leading end is to the right and the trailing end 208 is to the left. From this view, two new features can be seen that have not been previously discussed. One channel 228 and another channel 227 are shown in this view. The channel 228 has a height that is greater than its width while the channel 227 has a height that is smaller than that of the channel 228. Both of these channels have an opening exposed to the surface near the point where the trailing end 208 joins the posterior side 202. Furthermore, the channel 227 extends a significant portion around the circumference of the trailing end, substantially centered between the inferior side 211 and superior side 209, thereby exposing a portion of the interior of the other channel 228.

Figure 2E:
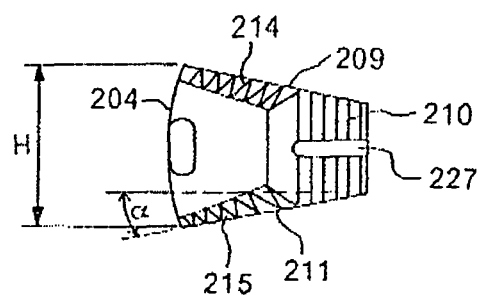

FIG. 2E depicts a view from the trailing end of the spacer 102 and shows one arrangement of the inferior side 211 and superior side 209. While the posterior side 202 and the anterior side 204 may be the same height, this design constraint is not necessary. In particular, the spacer of FIG. 2E includes an anterior side 204 that is taller than the posterior side 202. This causes the superior side 209 to slope upwardly from the posterior side 202 to the anterior side 204. Because, the anterior side also extends below the bottom of the posterior side 202, the inferior side 211 also slopes; in this instance it slopes downwardly from the posterior side 202 to the anterior side 204. One of ordinary skill will recognize that alternatively, either one of the superior or inferior sides could be arranged to have no slope, or an opposite slope, by sizing the anterior and posterior sides accordingly. Also, the slope of the superior and inferior sides does not necessarily have to be a constant value but may vary over its expanse. If the slope is constant, one exemplary value for that angle, α, is about 8 degrees.

The relative size of the spacer or height H, can vary according to its intended use. For example, the spacing between vertebrae may vary based on patient size and may also vary based on which region of the spine is being accessed. Thus, the nominal height, H, of the spacer may vary so as to provide a surgeon with a variety of different sized spacers. Exemplary spacer sizes that will accommodate most adult human situations include the following sizes. However, other sizes may be considered without departing from the scope of the present invention.

| H (inches) |
| --- |
| .278 |
| .315 |
| .354 |
| .394 |
| .433 |
| .472 |
| .512 |
| .561 |
| .591 |
| .630 |
| .668 |
| .709 |

Figure 2F:
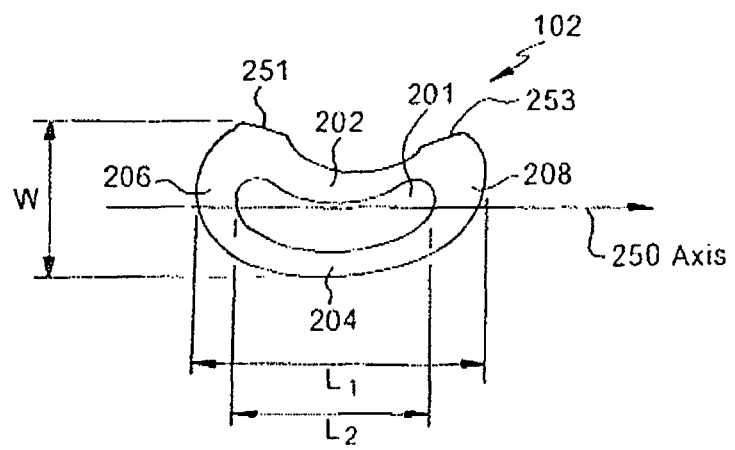

FIG. 2F depicts a view of the spacer similar to that of FIG. 2A. However, a number of the previously described features have been omitted so as not to obscure the axis 250 that extends in a direction substantially along the length of the spacer, $L_1$. For purposes of reference, this axis 250 is labeled the major axis of the spacer 102. Continuing with the example dimensions already provided, one exemplary spacer may have a length $L_1$ of approximately 1.06 inches and a width W of about 0.45 inches, while the cavity 201 may have a length $L_2$ of about 0.74 inches. These dimensions are provided as examples only of sizes that advantageously will fit many adult human patients of various sizes. One of ordinary skill will appreciate that other sizes and ratios of sizes may be used without departing from the scope of the present invention. Also depicted in this figure are relatively straight regions 251 and 253. In previously described spacers embodiments, the trailing end 208 and leading end 206 have been relatively arcuate in shape and transition smoothly into the posterior and anterior sides. However, the transition areas 251 and 253 may be straight rather than curved sections as shown in FIG. 2F.

Figure 3A:
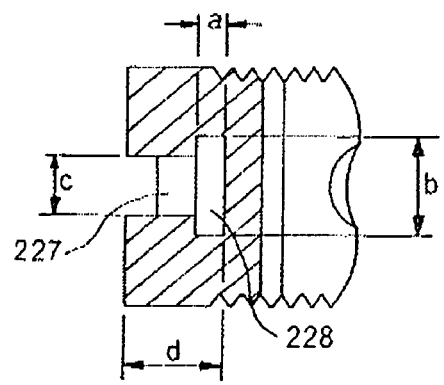
FIG. 3A depicts a detailed view of the trailing end of the spacer of FIG. 1.
Figure 3B:
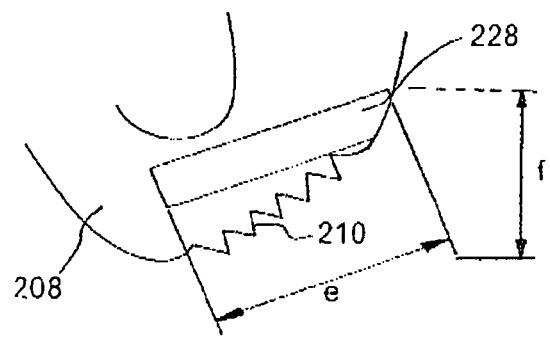
FIG. 3B depicts a detailed view of engaging surfaces of the trailing end of FIG. 3A.

An insertion tool for using with the spacer 102 is described later in more detail. However, FIGS. 3A and 3B depict portions of the trailing end 208 of the spacer 102 that interact with such an insertion tool. These features have been described earlier as the channels 227 and 228. The view of FIG. 3A is a cut-away view taken along the line A-A of FIG. 2A. This view shows the cross-sectional shape of the two channels 227 and 228. These channels 227 and 228 are shaped, sized and located to accept a portion of the insertion tool that extends outwardly from the insertion tool.

According to the sized spacers already discussed, the following dimensions provide channels that are appropriate for these spacers. However, these examples of channel sizes are merely exemplary in nature and other sized channels may be provided without departing from the scope of the present invention.

| Dimension | Size (inches) |
| --- | --- |
| a | .065 |
| b | .180 |
| c | .750 |
| d | .173 |
| e | .265 |
| f | .253 |

In FIG. 3B, more details about the engaging surfaces 210 can be seen. In particular, these engaging surfaces include a plurality of surfaces arranged radially along the exterior circumference of the trailing end 208. As explained later, complementary-shaped engaging surfaces on an insertion tool may engage different groups of these surfaces 210 so that an angle formed between the tool and the spacer may vary based on which of the engaging surfaces 210 are aligned with the complementary surfaces of the tool.

Figure 4A:
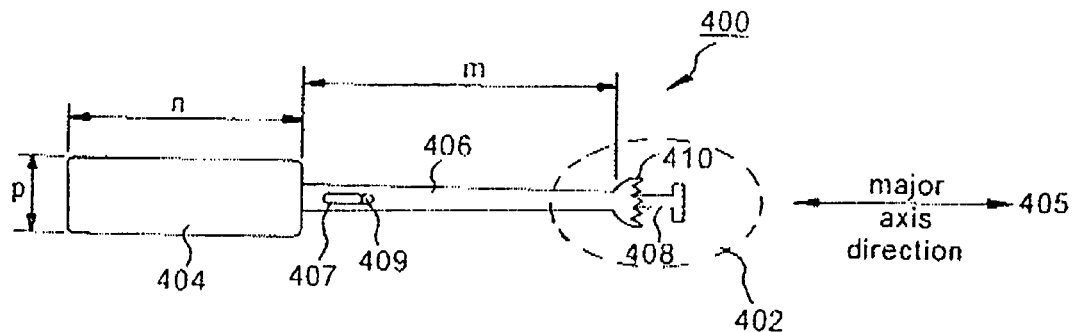
FIG. 4A depicts a view of an insertion tool in accordance with the principles of the present invention.
Figure 4B:
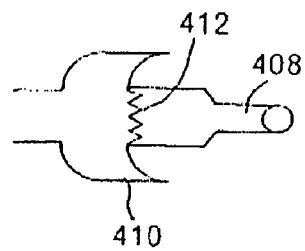
FIGS. 4B and 4C depict a detailed view of the extending portion of the tool of FIG. 4A.
Figure 4C:
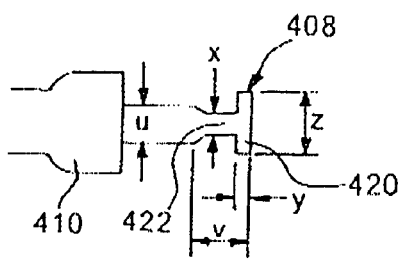

FIGS. 4A-4C depict an insertion tool 400 and its details. In particular, FIGS. 4B and 4C depict a detailed view of the region 402 in FIG. 4A. The insertion tool 400 includes a handle portion 404 and a shaft 406 extending towards an end distant from the handle 404. This distal end is generally referred to as the insertion end of the tool 400 and includes a surface 410 shaped to engage the features 210 on the trailing end of the spacer 102. The insertion end also includes an extending portion 408 that extends outwardly from the handle 404 of the tool. For many surgeons, sizing the tool so that p is approximately 1.13 inches, n is 5.4 inches and m is 7.4 inches will result in a comfortable tool. Of course, other sizes and ratios are also contemplated within the scope of the present invention.

Conceptually, the handle 404 operates to move the surface 410 towards or away from the extending portion 408. In operation, this may be accomplished by moving either the extending portion 408 or the surface 410; in either case the same relative motion is accomplished. One exemplary technique is for the extending portion 408 to be attached to a shaft that is located within the shaft 406. Twisting the handle 404 in one direction causes the outside shaft 406 to move relative to the inner shaft (not shown). This movement causes the surface 410 to move towards the extending portion 408. Rotation of the handle 404 in the opposite direction causes opposite movement of the outside shaft 406 resulting in motion of the surface 410 away from the extending portion 408. In an exemplary embodiment, the inner shaft includes a stop 409 that extends through an opening 407 so as to align the shafts and restrict the extent of movement of the outside shaft 406 in either direction of travel.

FIG. 4B depicts a detailed top view of the distal end of the insertion tool 400. From this view, the engaging features 412 of the surface 410 are visible. These features 412 are shaped to engage the similarly shaped features 210 on the trailing end of the space 102. The detailed side view of FIG. 4C obscures these features 412 but depicts the extending portion 408 from a perspective that allows exemplary measurements to be provided. The measurements provided herein are exemplary in nature and are intended to match to the spacer sizes that have been previously described. One of ordinary skill will recognize that different sized spacers 102 and different sized channels 227, 228 will result in different sized extending portions 408. Exemplary measurements include:

| Dimension | Size (inches) |
|---|---|
| u | 0.13 |
| v | 0.18 |
| x | 0.06 |
| y | 0.04 |
| z | 0.16 |

In operation, the portion 422 of the extending portion 408 is inserted into and fits within the channel 227 of the spacer 102. The other portion 420 is inserted within the other channel 228. In this way, the extending portion 408 securely engages the spacer 102 because the portion 420 is too large to pass through the channel 227. From this position, the surface 410 may be moved so as to be positioned closer to the extending portion 408. More particularly, the surface 410 is moved in this direction so that the engaging features 412 engage complementary-shaped features 210 on the spacer's trailing end 208.

When the engaging features 412 and 210 are engaged to one another, then the insertion tool 400 and the spacer 102 are securely, but releasably, fastened to one another such that relative motion between the two is prevented. When the engaging features are not actively engaged, the tool 400 and the spacer 102 are still securely engaged (through operation of the extending portion 408); however, relative motion is permitted because the spacer 102 can rotate around the portion 420 of the extending portion 408.

This rotation allows the spacer 102 and the tool to be repositioned so that the engaging features 412 of the tool 400 can be aligned to engage different complementary-shaped features 210 of the spacer. As a result, an angle between the major axis 405 of the tool 400 and the spacer's 250 can be changed even while the extending portion 408 is disposed within the spacer 102.

Figure 5A:
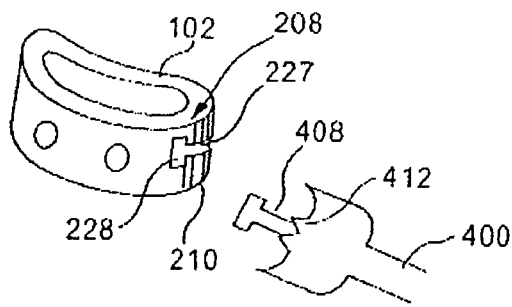
FIGS. 5A-5C depict a series of views of an insertion tool engaging a spacer in accordance with the principles of the present invention.
Figure 5B:
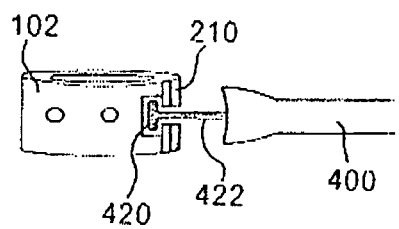
Figure 5C:
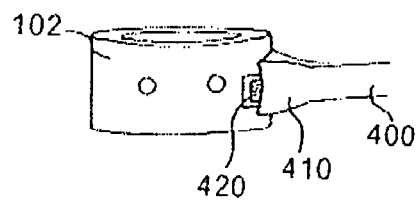

FIGS. 5A-5C depict the series of events just described. The spacer 102 of these figures may include all the features previously described with relation to earlier figures. However, these features have not been explicitly depicted so as not to obscure the events shown in FIGS. 5A-5C. In FIG. 5A the tool 400 has its extending portion 408 extended as it approaches the trailing end 208 of the spacer 102. In particular, the channels 227, 228 and the engaging features 210 are shown as well as the tool's engaging features 412. During surgery, the spacer 102 may already be placed in a patient's body at this time by some other means or may be outside of the patient's body being prepared for insertion with the tool 400.

In FIG. 5B, the portion 420 of the extending portion 408 has been inserted in the channel 228 and the other portion 422 has been inserted into the channel 227 and extends outwardly from the spacer 102. Next, as shown in FIG. 5C, the surface 410 of the tool is moved in a relative direction towards the spacer 102 so that the engaging surfaces 210 and 412 actively engage and couple with one another. These complementary-shaped engaging surfaces are depicted in these figures as pointed teeth. However, other shapes that actively engage one another may be used as well. For example, other shaped teeth may be used such as cog-shaped teeth as well as rounded over teeth may be used as well.

Figure 6A:
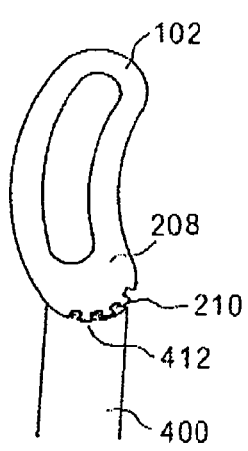
FIGS. 6A-6C depict an insertion tool and a spacer engaged in three different positions in accordance with the principles of the present invention.
Figure 6B:
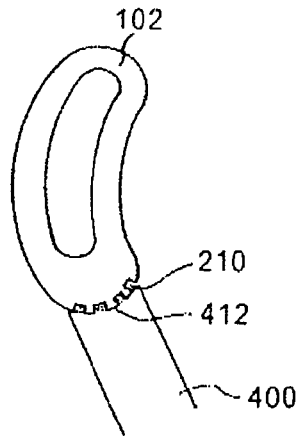
Figure 6C:
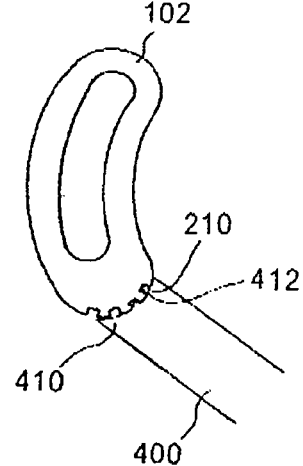

FIGS. 6A-6C depict the alignment of the tool 400 and the spacer 102 in three different positions. The different positions relate to which of the engaging features 210 of the spacer 102 align with the engaging features 412 of the tool. For simplicity, these engaging features 210, 412 will be referred to as "teeth" although other shapes are contemplated as well.

In FIG. 6A the teeth of the tool engage the teeth of the spacer 102 that are closer to the anterior side 204. The opposite is true in FIG. 6C where the teeth closer to the posterior side 202 are engaged. FIG. 6B depicts a position between these two extremes. The number of teeth 210 around the trailing end of the spacer 102 is a factor in the number of different possible positions in which the tool 400 and the spacer 102 can be engaged. For example, the teeth 210 may extend for an arc that measures about +/−35 degrees from the center of the trailing end 208. Other ranges, both smaller and larger, are contemplated as well. The teeth 412 on the tool are preferably fewer in number than those 210 on the spacer 102.

Also, the spread of the teeth 412 may be less as well on the tool 400, such as about +/−20 degrees from the center of the tool's surface 410.

Because of the arrangement of the teeth 210, 412 and the extending portion 408, the tool 400 may be moved between the different positions of FIGS. 6A-6C while the portion 420 remains within the channel 228. The surface 410 is simply moved away from the spacer 102 so that the engaging surfaces 210, 412 are disengaged and then the major axis 405 of the tool 400 may be rotated relative to the spacer 102. Thus, the tool 400 and the spacer 102 may remain securely attached to one another, while still allowing realigning of the angle formed between the major axis 250 of the spacer 102 and that of the tool 400. When a new, desired alignment is reached, the engaging surfaces 210, 412 may be re-engaged in a secure manner by moving the surface 410 towards the spacer 102.

As a result, a surgeon may alter the insertion angle of the spacer 102 during surgery in numerous and various ways to account for possible variations and conditions that might arise during surgery. Even though such flexibility is provided, the tool 400 and the spacer 102 remain fastened together so that re-securing the two relative to one another, after an adjustment, may be easily accomplished without difficulty or fear of unwanted separation.

Figure 7:
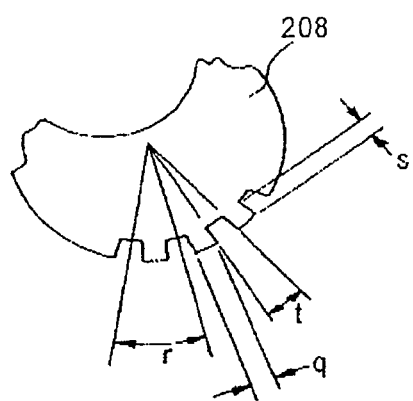

FIG. 7 depicts a detailed view of gear-shaped teeth along with exemplary dimensions for a spacer. The trailing end 208 depicted in FIG. 7 includes, for example 3 gear-shaped teeth. One of ordinary skill will recognize that different shaped teeth may be used as well as differently sized teeth. Some of the dimensions that define teeth are the angles formed by their adjacent sides, the sizes of the valleys between the teeth, the height of the teeth, and the width of the teeth. The table below provides exemplary dimensions for teeth sized to fit the previously described spacers for a typical human patient.

| Dimension | Size |
|-----------|------|
| q | .023 inches |
| r | 40 degrees |
| s | .030 inches |
| t | 25 degrees |

These specific dimensions are approximate in nature and may vary significantly without departing from the spirit and scope of the present invention.

Figure 8A:
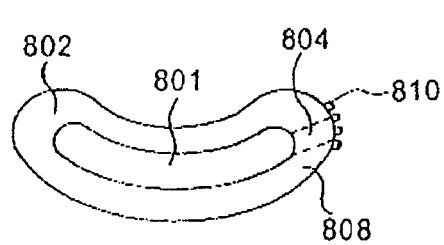
FIGS. 8A-8C depict an alternative intervertebral spacer.
Figure 8B:
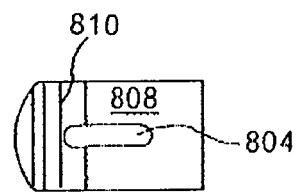
Figure 8C:
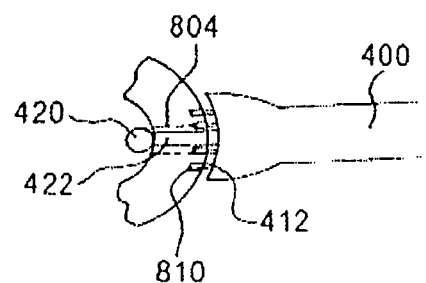

FIGS. 8A-8C depict an alternative spacer 802 that performs functionally equivalent to the previously described spacer 102. In particular, the alternative spacer 802 includes a trailing end 808 that includes engaging features 810. The engaging features 810 are substantially the same as those described previously. However, instead of the channels 227 and 228, the trailing end 808 includes a through hole 804 that extends through from the exterior surface of the trailing end 808 to the central cavity 801. The shape of the hole 804, shown in FIG. 8B, is such that it accepts the insertion of the portion 420 of the extending portion 408 in one orientation but prevents removal of the portion 420 back through the opening 804 when the portion 420 is rotated relative to the opening of the hole 804. As seen in FIG. 8C, the engaging surfaces 810 and 412 engage in a manner similar to that already described while one portion 422 of the extending portion 408 resides in the through hole 804 and the other portion 420 of the extending portion 408 is trapped within the cavity 801 of the spacer 802. Similar to before, the angle of the tool 400 and the spacer 802 may be changed while the portion 420 remains in position. This is accomplished merely by disengaging the engaging features of the tool 400 and the spacer 802 and repositioning the tool 400 relative to the spacer 802.

FIGS. 9A-9C depict another alternative intervertebral spacer and insertion tool. According to this alternative, the trailing end 908 of the spacer 902 has a partially cylindrical channel that is shaped to interact with the insertion tool 950. The channel can also be considered as semicircular in nature as well. In FIG. 9A, a view from the top of the spacer 902, the channel is shown as dotted region 901. The side view of FIG. 9B also illustrates the placement of the channel 901 relative to the trailing end 908 having engaging teeth 910. While it is not necessary to form the channel 901 as a complete cylinder, or circle, encompassing an entire 360 degrees, the channel 901 advantageously has an arcuate circumference that encompasses at least 180 degrees. The larger the arcuate circumference is, the greater the number of positions at which the insertion tool may securely attach to the implant 902. However, the structure of the implant 902 at its trailing end 908 should remain strong enough to perform its function and, therefore, the arctuate circumference is limited by practical considerations. As shown, the channel 901 is located between an upper edge 907 and a lower edge 905 of the trailing end 908 of the implant 902. As for the channel size, one exemplary height may be approximately 0.135 inches although other sizes are contemplated as well.

The insertion tool 950 of FIG. 9C includes engaging features 952 similar to those previously described but includes a different extending portion having two opposing arms 954 and 956. These arms 954, 956 are shaped to be inserted within the channel 901 to grip the exterior cylindrical surface of the channel 901. Because of the arcuate range of the channel 901, the arms 954, 956 can securely grip within the channel at a number of different positions. The arms 954 may be formed of a resilient plastic or metal that is well-suited for the intended surgical environment. Also, the arms 956, 954 have, respectively, angled portion 958, 960 that cause the arms 954, 956 to be forced together when the engaging features 952 are moved toward the trailing end of a spacer. Furthermore, the relative distance between the arms 954, 956 may be designed such that the engaging features 952 and 910 may be slightly separated from active engagement while the arms 954, 956 remain in contact with the external surface of the channel 901. In this manner, the position of the tool 950 relative to the spacer 902 may be changed while the two remain in relatively secure engagement.

Figure 10A:
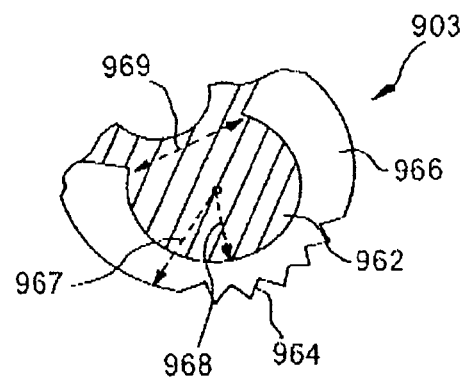
FIGS. 10A and 10B depict a detailed view of different embodiments of the alternative intervertebral spacer of FIGS. 9A and 9B.
Figure 10B:
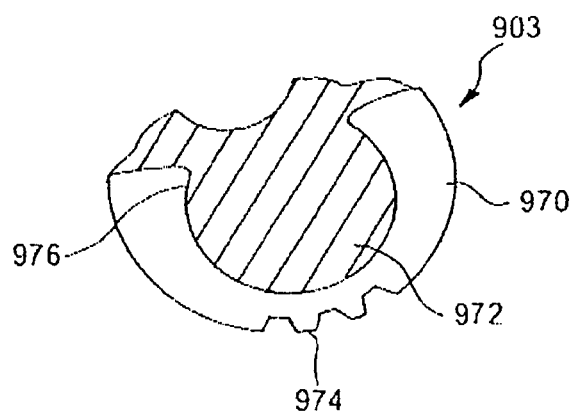

FIGS. 10A and 10B offer a more detailed view of the region 903 of FIG. 9A. As described, the trailing end 908 of the implant 902 has a channel 966 that is formed around a cylindrical or semicircular portion 962. The radius 968 of the semicircular portion 962 may, for example, be approximately 0.11 inches and the outside radius 967 of the trailing end 908 may, for example, be larger such as approximately 0.1618 inches. Thus, the channel 966 has a thickness that varies because of these different radii 967, 968. The teeth 964, or engaging portion, operated to securely engage complimentary features of the insertion tool (not shown) so that the insertion tool and the spacer may be securely engaged at any of a plurality of different positions and angles.

The semicircular portion 962 terminates at two ends that are separated by a distance 969. In the particular example provided above, with the particular radii 967, 968, the distance 969 may be, for example, approximately 0.1850 inches. This distance depends on the arcuate circumference of the semicircular portion 962 which may vary anywhere from 180 to about 250 degrees.

FIG. 10B depicts an alternative detailed view of region 903 that has many similarities to FIG. 10A such as the channel 970 and the semicircular portion 972. However, the engaging surfaces 974 may be cog-like teeth rather than the sharp teeth 964 of FIG. 10A. Additionally, the semicircular portion 972 does not necessarily have to have a uniform radius of curvature but may also include a portion 976 that has a different radius of curvature. The portion 976 may be present on both ends of the portion 972 or just at a single end.

Figure 11A:
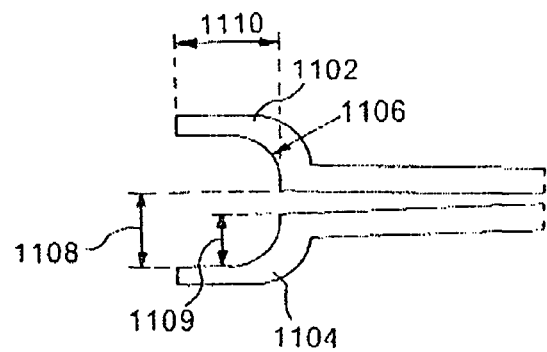
FIGS. 11A and 11B depict a detailed view of portions of the insertion tool adapted to operate with the alternative intervertebral spacer of FIGS. 9A and 9B.
Figure 11B:
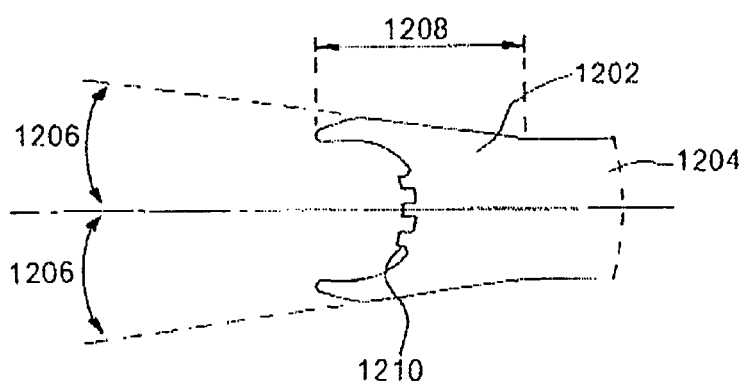

FIG. 11A depicts a detailed view of an insertion tool of FIG. 9C that is adapted to securely engage the spacer of FIGS. 9A and 9B at a plurality of different positions and angles. FIG. 11A depicts the opposing arms that are adapted to engage the channel of the spacer while FIG. 11B depicts the engaging end of the insertion tool that has an engaging surface that includes engaging features that match complimentary features on the upper and lower edges of the trailing end of the spacer.

As mentioned earlier, the opposing arms 1102, 1104 are resiliently arranged so that they separate from one another when extender from the tool 950 and squeeze towards one another when retracted into the tool 950. The arms 1102, 1104 are shaped and sized to securely fit within the channel 901 of the spacer 902. Thus, for example, given the dimension described with relation to FIGS. 10A and 10B, the features of the opposing arms 1102, 1104 may have the following dimensions.

| Dimension | Size |
|---|---|
| 1106 | Radius of .1117 inches |
| 1108 | .125 inches |
| 1109 | .110 inches |
| 1110 | .187 inches |

These dimensions are exemplary in nature and are provided merely as a specific example of one embodiment of the variety of different spacers and insertion tools contemplated within the scope of the present invention.

The portion 1202 of the tool 950 is the external part of the end of the tool through which the opposing arms 1102, 1104 extend. Typically, there is a first portion 1202 that engages the trailing end 908 of the spacer 902 that eventually merges into a shaft portion 1204 of the insertion tool. The first portion 1202 may, for example, have a length of approximately 0.30 inches although this length may, of course, be larger or smaller as well. The first portion 1202 is shaped to fit around the trailing end 908 of the spacer 902 and, therefore, is curved in nature to match the curvature of the spacer 902. For example, the first portion 1202 can converge outwardly at a rate 1206 of 11 degrees from a centerline such that the curvature of the first portion 1202 can accommodate the spacer 902. Of particular importance are the engaging features 1210 that are configured to engage complimentary features 910 on the upper edge 907 and lower edge 905 of the spacer 902. Depending on which complementary features 910 are engaged, the angle of engagement between the tool and the spacer can vary. In this way, the tool and the spacer may securely engage one another at one of many different, selectable engagement angles. The height of the engaging surfaces 1210 may, for example, be approximately 0.023 inches.

The tool 950 may be positioned such that the opposing arms 1102, 1104 are located within the channel 966 around the semicircular portion 962. As the first portion is extended (relative to the opposing arms) towards the spacer 902, the opposing arms are forced together so that they grip the exterior surface of the semicircular portion 962. Even though the tool 950 and spacer 902 are somewhat securely engaged at this point, the tool 950 can still be twisted relative to the spacer 902 because the mechanical force applied to the tool 950 by a doctor can overcome the frictional engagement between the opposing arms 1102, 1104 and the channel 966. Thus, the angle between the tool 950 and the spacer 902 can be adjusted even though the tool 950 and spacer 902 are connected in a manner in which they will not inadvertently separate. Eventually, the engaging surfaces 1210 will engage complementary surfaces 910 on the spacer 902. At this point, the angle between the tool 950 and the spacer 902 will be fixed in one of the many different selectable angles that are possible. To reposition the tool 950 at a different angle, the first portion 1202 is refracted from the spacer so that the engaging surfaces of the tool and spacer disengage. The tool 950 can once again be twisted relative to the spacer 902 so that when they are reengaged they are at a different angle relative to one another.

Figure 12A:
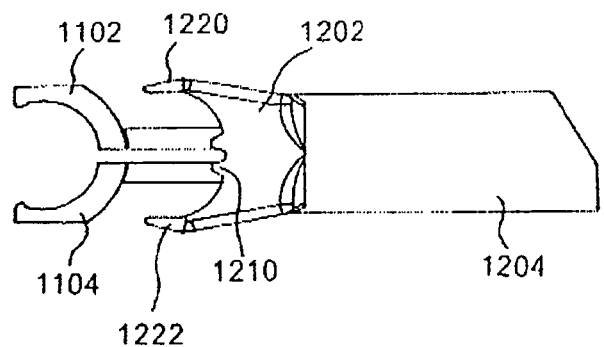
FIGS. 12A and 12B depict other views of the insertion tool of FIGS. 11A and 11B.
Figure 12B:
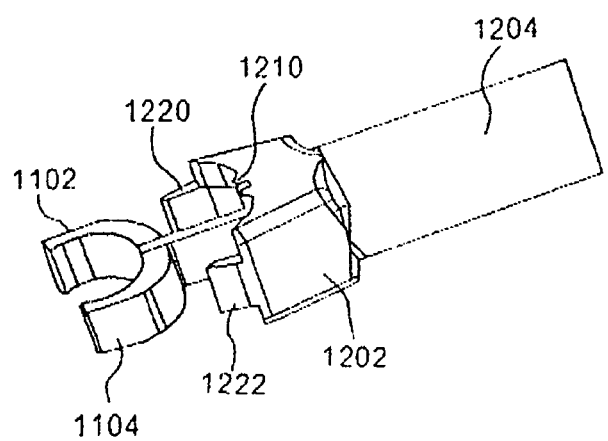

FIGS. 12A and 12B depict other views of the insertion tool of FIGS. 11A and 11B that help highlight some of the features of this insertion tool. As explained earlier, the opposing arms 1102, 1104 in an unbiased position (e.g., FIGS. 12A and 12B) are separated from one another. However, as the opposing arms 1102, 1104 and the external portion 1202 move relative to one another so the external portion 1202 moves over the opposing arms 1102, 1104, these arms are pressed towards one another in order to grip the spacer. In particular, these arms 1102, 1104 are shaped to be inserted in the channel of the spacer and then tighten around that cylindrical surface. Unlike the insertion tool of FIG. 9C, the tool of FIGS. 12A and 12B relies on features of the external portion 1202 to press the opposing arms 1102, 1104 together.

In particular, the external portion 1202 includes wings, or arms, 1220, 1222 that are shaped so that they contact the opposing arms 1102, 1104 and squeeze these arms 1102, 1104 together. Thus, when the opposing arms 1102, 1104 are withdrawn back towards the external portion 1202, the outside surfaces of the arms 1102, 1104 come in contact with a respective wing 1220, 1222 which forces the opposing arms 1102, 1104 in a direction towards one another. When the opposing arms 1102, 1104 are extended outwardly from the external portion 1202, they are free to expand once they clear the wings 1220, 1222. As the opposing arms 1102, 1104 transition form the "open" to the "closed" position, the grip on the spacer becomes tighter and more secure. Between the two positions of "open" and "closed" there is a range of intermediate positions where the insertion tool securely grips the spacer but still permits rotation of the tool relative to the spacer.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A kidney-shaped intervertebral spacer comprising:
 a leading end;
 a trailing end comprising an engaging portion configured to engage complementary engaging features of an insertion tool at a plurality of engagement positions, a channel configured to accept an extending portion of the insertion tool, and a partially cylindrical portion within the channel;
 a superior side extending substantially from the leading end to the trailing end; and
 an inferior side, opposite the superior side, extending substantially from the leading end to the trailing end;
 wherein the channel is disposed between and separated from the superior and inferior sides; and
 wherein the partially cylindrical portion is positioned in the recessed channel between the superior side and the inferior side, and is configured to be gripped by the extending portion of the insertion tool.

2. The intervertebral spacer of claim 1, further comprising:
 an anterior side connecting the leading end and the trailing end; and
 a posterior side opposite the anterior side and connecting the leading end and the trailing end;
 wherein the anterior side, the posterior side, the leading end, and the trailing end are arranged to form a cage having a cavity.

3. The intervertebral spacer of claim 1, further comprising:
 an anterior side connecting the leading end and the trailing end;
 a posterior side opposite the anterior side and connecting the leading end and the trailing end;
 wherein the superior side is generally planar; and
 wherein the inferior side is generally planar;
 wherein a first height of the anterior side is greater than a second height of the posterior side such that the superior side slopes downwardly from the anterior side to the posterior side.

4. The intervertebral spacer of claim 1, further comprising:
 an anterior side connecting the leading end and the trailing end;
 a posterior side opposite the anterior side and connecting the leading end and the trailing end;
 wherein the superior side is generally planar; and
 wherein the inferior side is generally planar;
 wherein a first height of the anterior side is less than a second height of the posterior side such that the inferior side slopes upwardly from the anterior side to the posterior side.

5. The intervertebral spacer of claim 1, wherein:
 the superior side is generally planar; and
 the inferior side is generally planar.

6. The intervertebral spacer of claim 1, further comprising a major axis from the leading end to the trailing end, and wherein the engaging portion comprises a plurality of teeth configured to engage the complementary engaging features of the insertion tool in the plurality of engagement positions, wherein an angle between the major axis and a shaft of the insertion tool differs at each of the engagement positions.

7. The intervertebral spacer of claim 6, wherein the partially cylindrical portion is configured to be gripped by the extending portion of the insertion tool when the plurality of teeth engage the complementary engaging features of the insertion tool.

8. The intervertebral spacer of claim 6, wherein the engaging portion of the trailing end is generally arcuate.

9. The intervertebral spacer of claim 1, wherein the intervertebral spacer is configured such that the complementary engaging features of the insertion tool can be disengaged from the engaging portion of the intervertebral spacer while the extending portion is disposed within the channel.

10. The intervertebral spacer of claim 9, wherein the trailing end is configured such that the extending portion remains in contact with the partially cylindrical portion while the engaging features of the insertion tool are disengaged from the engaging portion of the intervertebral spacer.

11. The intervertebral spacer of claim 1, wherein the partially cylindrical portion has an arcuate circumference of at least 180 degrees.

12. The intervertebral spacer of claim 1, wherein the trailing end is configured such that the extending portion of the insertion tool can be engaged with the partially cylindrical portion while the shaft of the insertion tool remains between planes that are coincident with an inferior side and a superior side of the intervertebral spacer.

13. The intervertebral spacer of claim 1, wherein the trailing end is configured such that the insertion tool can be engaged with the engaging portion and can extend into the channel while the shaft remains between planes that are coincident with an inferior side and a superior side of the intervertebral spacer.

14. A kidney-shaped intervertebral spacer comprising:
 a superior side and an inferior side opposite the superior side;
 a posterior side and an anterior side;
 a leading end; and
 a trailing end comprising an engaging portion, a channel, and a partially cylindrical portion disposed within the channel;
 wherein a major axis of the spacer extends between the leading end and the trailing end,
 wherein the engaging portion is shaped to engage a complementary-shaped portion of an insertion tool having a shaft at a plurality of positions such that an angle of the shaft with respect to the major axis differs for each of the positions, and
 wherein the superior side extends substantially from the leading end to the trailing end;
 wherein the inferior side extends substantially from the leading end to the trailing end;
 wherein the channel is disposed between and separated from the superior and inferior sides, and is configured to accept an extending portion of the insertion tool; and
 wherein the partially cylindrical portion is positioned in the channel between the superior side and the inferior side, and is configured to be gripped by the extending portion of the insertion tool.

15. The intervertebral spacer of claim 14, wherein the trailing end is configured to allow the insertion tool to be disengaged from a first position and re-engaged at a second position while the extending portion remains disposed within the channel.

16. The intervertebral spacer of claim 14, wherein the trailing end is configured such that the insertion tool can be engaged with the engaging portion and the partially cylindrical portion while the shaft remains between a pair of planes that are coincident with the inferior and superior sides.

17. An intervertebral spacer comprising:
a leading end;
a trailing end;
a convex anterior side connecting the leading end and the trailing end;
a concave posterior side opposite the anterior side and connecting the leading end and the trailing end;
a superior side connecting the leading end and the trailing end;
a inferior side opposite the superior side connecting the leading end and the trailing end;
wherein the trailing end comprises (a) a recessed channel between the superior side and the inferior side, (b) a superior engaging portion between the superior surface and the recessed channel, and (c) an inferior engaging portion between the inferior surface and the recessed channel;
wherein a cylindrical portion having an exterior cylindrical surface is positioned in the recessed channel between the superior engaging portion and the inferior engaging portion such that the exterior cylindrical surface is recessed from the superior engaging portion and the inferior engaging portion, the cylindrical portion comprising an arc of at least 180 degrees.

18. The spacer of claim 17, wherein the arc of the cylindrical portion is less than 360 degrees.

19. The spacer of claim 17, wherein the cylindrical portion has a cylinder outer radius and the trailing end of the spacer has a spacer outer radius, and the cylinder outer radius is smaller than the spacer outer radius.

20. The spacer of claim 19, wherein the cylindrical portion has a non-uniform radius of curvature.

21. The spacer of claim 17, wherein the spacer comprises a cavity therethrough, connecting the superior surface and the inferior surface.

22. The spacer of claim 17, wherein a first height of the anterior side is greater than a second height of the posterior side such that the superior surface slopes downwardly from the anterior side to the posterior side.

23. The spacer of claim 17, wherein the superior engaging portion and the inferior engaging portion comprise respective spacer engaging features.

24. The spacer of claim 23, wherein the spacer engaging features comprise teeth.

25. The spacer of claim 24, wherein the spacer engaging features comprise teeth that have flats.

* * * * *